United States Patent [19]

Evers et al.

[11] Patent Number: 5,077,274

[45] Date of Patent: Dec. 31, 1991

[54] BICYCLO[10.2.0]TETRADECAN-13-ONE, FRAGRANCE USE THEREOF, PROCESS FOR PREPARING SAME AND DICHLORINATED INTERMEDIATE USED IN SAID PROCESS

[75] Inventors: William J. Evers, Atlantic Highlands; Howard H. Heinsohn, Jr., Freehold, both of N.J.

[73] Assignee: International Flavors & Fragrances Inc., New York, N.Y.

[21] Appl. No.: 596,506

[22] Filed: Oct. 12, 1990

[51] Int. Cl.$^5$ .............................................. A61K 7/46
[52] U.S. Cl. ..................................... 512/15; 568/374; 568/304
[58] Field of Search ........................... 568/374; 512/15

[56] References Cited

U.S. PATENT DOCUMENTS

| | | | |
|---|---|---|---|
| 3,465,040 | 9/1969 | Nozaki et al. | 568/374 |
| 3,966,819 | 6/1976 | Schulte-Elte et al. | 568/374 |
| 4,301,303 | 11/1981 | Hoffman et al. | 568/375 |

FOREIGN PATENT DOCUMENTS

| | | | |
|---|---|---|---|
| 2630428 | 1/1978 | Fed. Rep. of Germany | 568/374 |
| 1205050 | 9/1970 | United Kingdom | 508/374 |
| 1422089 | 1/1976 | United Kingdom | 568/374 |

OTHER PUBLICATIONS

Danheiser et al., Tet Letters, vol. 28, pp. 3294–3302 (1987).
Mehta and Rao, "Ultrasound Promoted Dichloroketene-Olefin Cycloadditions", Synthetic Communications, 15(11), 991–1000, (1985).
Mehta dn Rao, "Strategy for Cyclopentenone Annulation of Olefins:A General Protocol for Bicyclo[n.3.0]Enone Synthesis", Tetrahedron Letters, vol. 25, No. 17, pp. 1839–1842, 1984.

*Primary Examiner*—James H. Reamer
*Attorney, Agent, or Firm*—Arthur L. Liberman

[57] ABSTRACT

Described is the novel compound, bicyclo[10.2.0]tetradecan-13-one having the structure:

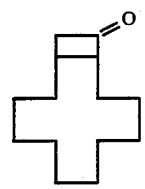

as well as the use thereof in augmenting or enhancing the aroma of consumable materials including perfume compositions, colognes and perfumed articles (including solid or liquid anionic, cationic, nonionic or zwitterionic detergents, fabric softeners, cosmetic powders and hair preparations). Also described is a process for preparing said bicyclo[10.2.0]tetradecan-13-one using as a reaction intermediate the compound having the structure:

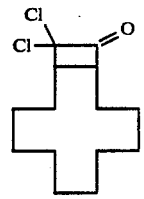

4 Claims, 7 Drawing Sheets

GLC PROFILE FOR EXAMPLE I.

GC-MASS SPECTRUM FOR EXAMPLE I.

IR SPECTRUM FOR EXAMPLE I.

GLC PROFILE FOR EXAMPLE II.

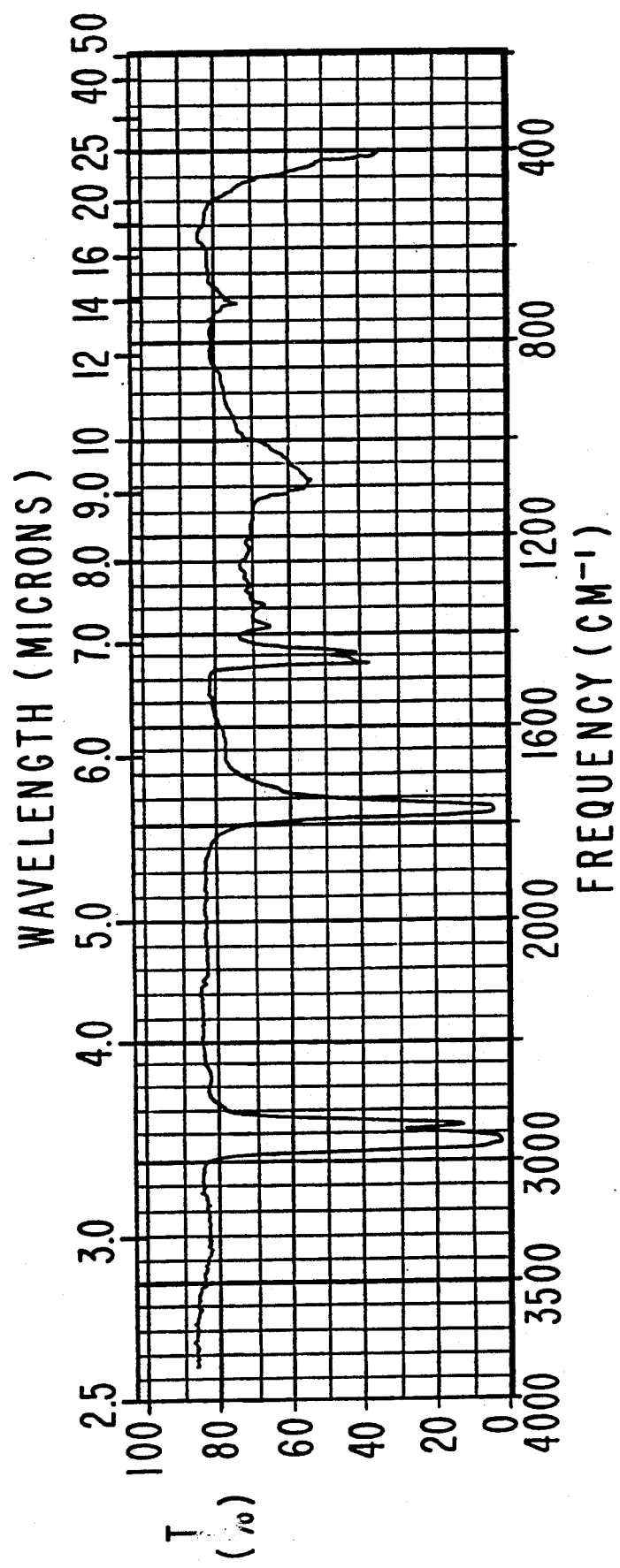

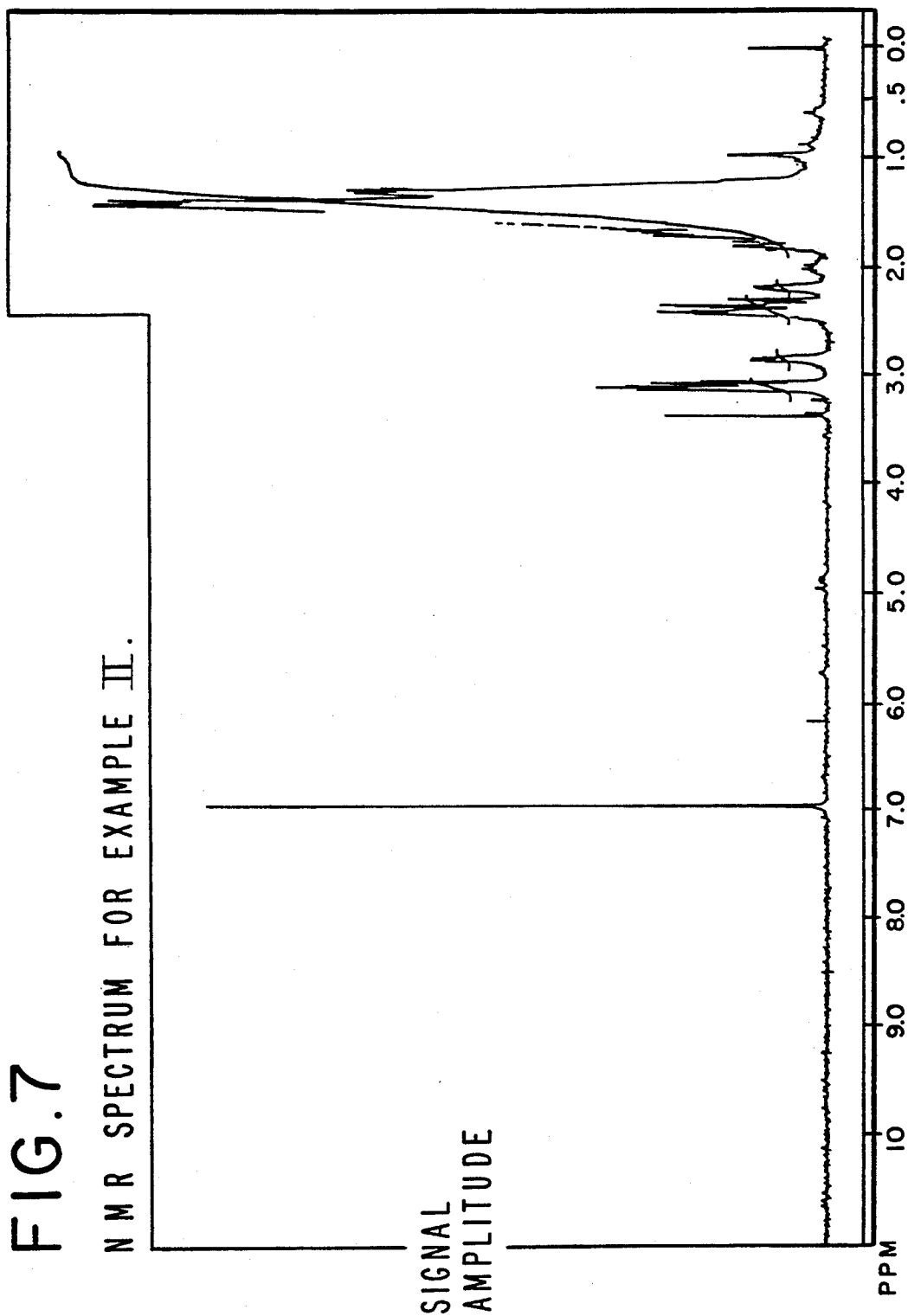
FIG.7 NMR SPECTRUM FOR EXAMPLE II.

BICYCLO[10.2.0]TETRADECAN-13-ONE, FRAGRANCE USE THEREOF, PROCESS FOR PREPARING SAME AND DICHLORINATED INTERMEDIATE USED IN SAID PROCESS

BACKGROUND OF THE INVENTION

Materials which can provide musky and earthy aromas with minty, green and camphoraceous topnotes, particularly those materials which are relatively inexpensive are highly sort after in the art of perfumery. Many of the natural materials which provide such fragrance profiles and contribute such desired nuances to perfume compositions and perfumed articles are high in cost, vary in quality from one batch to another and/or are generally subject to the usual variations of natural products.

There is, accordingly, a continuing effort to find synthetic materials which will replace the essential fragrance notes produced by natural essential oils or compositions thereof. Unfortunately, many of these synthetic materials either have the desired nuances only to a relatively small degree of else contribute undesirable or unwanted odor to the composition. The search for materials which can provide a more refined musky and earthy aroma with minty, green and camphoraceous topnotes has been difficult and relatively costly in the areas of both natural products and synthetic products.

The prior art, for example, U.S. Letters Patent 4,301,303 discloses cyclododecyl ketone derivatives, for example, those having the structures:

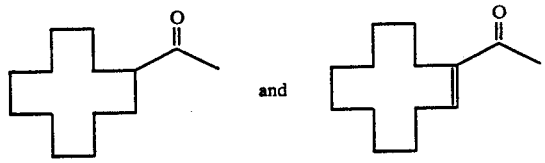

The structures of the compounds of the prior art are different in kind from the structure of the compound to wit:

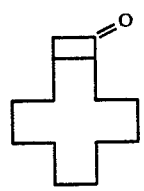

The properties for the compound having the structure:

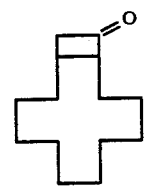

with respect to perfume utilities are unexpected, unobvious and advantageous when compared to the compounds having the structures:

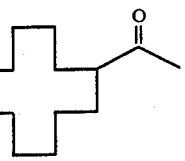 and 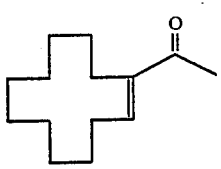

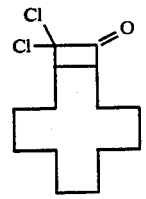

(Conditions: 30 Meters×0.32mm fused silica capillary SPB-1 column programmed at 120°–225° C. at 8° C. per minute).

Figure 2:
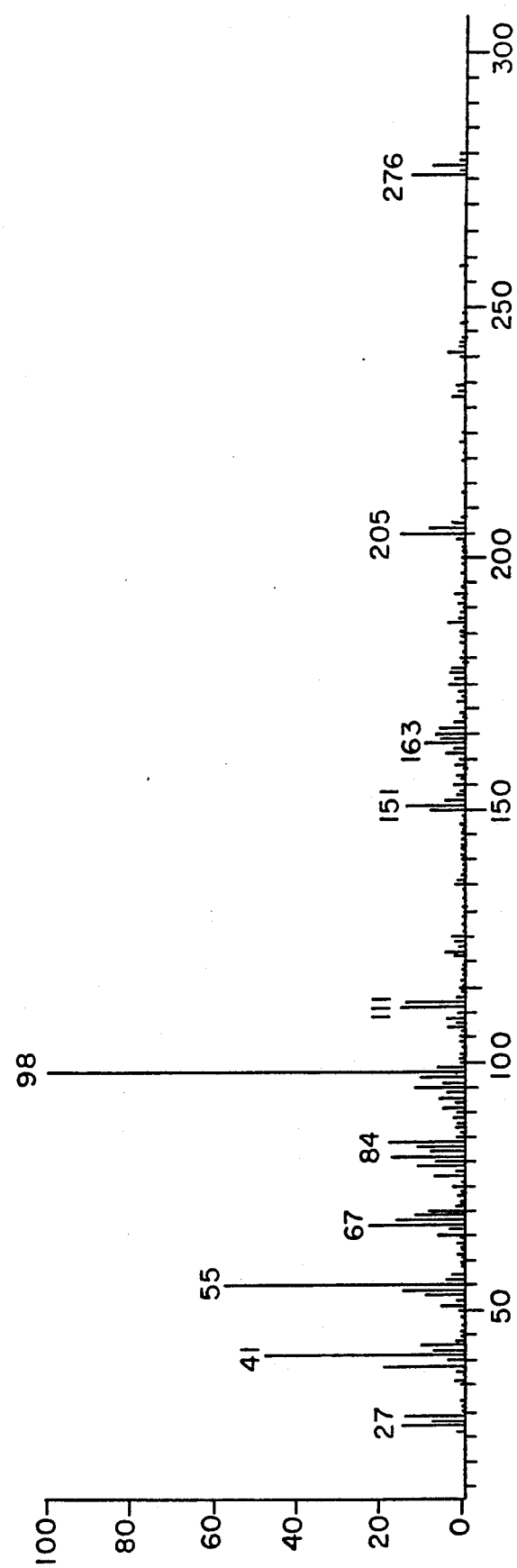

FIG. 2 is the GC-mass spectrum for the compound having the structure:

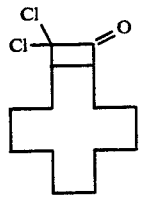

produced according to Example I.

Figure 3:
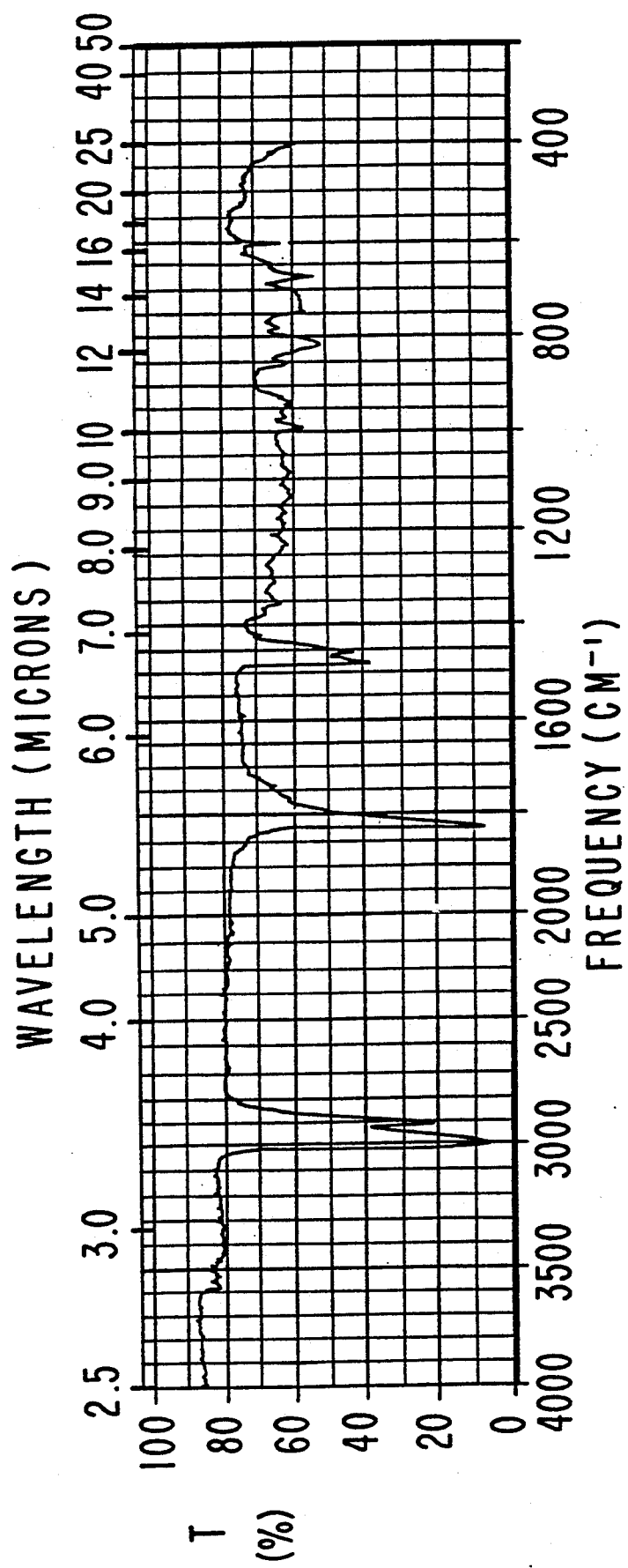

FIG. 3 is the infra-red spectrum for the compound having the structure:

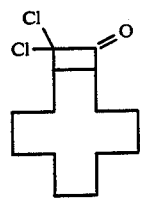

prepared according to Example 1.

Figure 4:
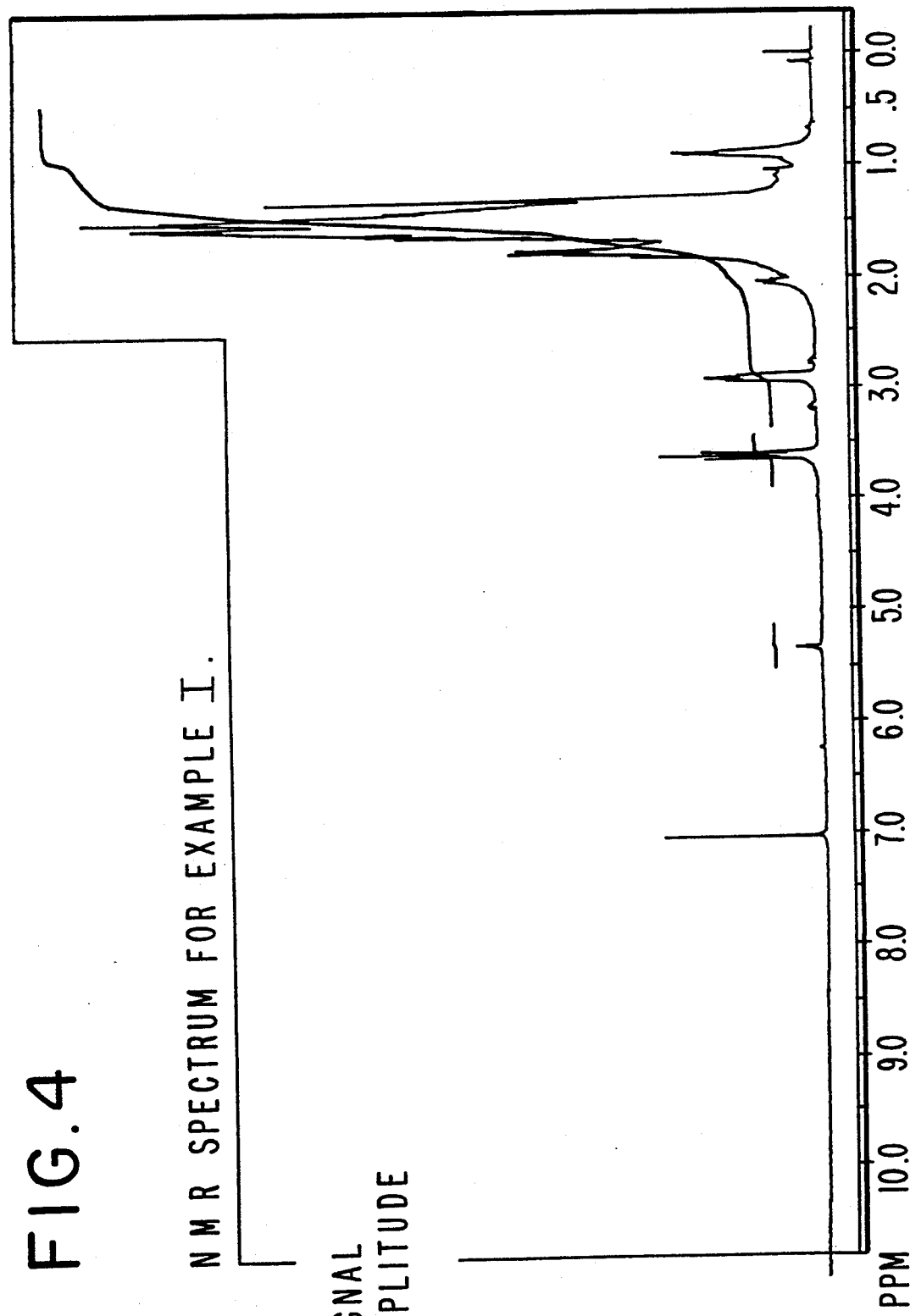

FIG. 4 is the NMR spectrum for the compound having the structure:

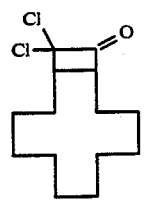

prepared according to Example I.

Figure 5:
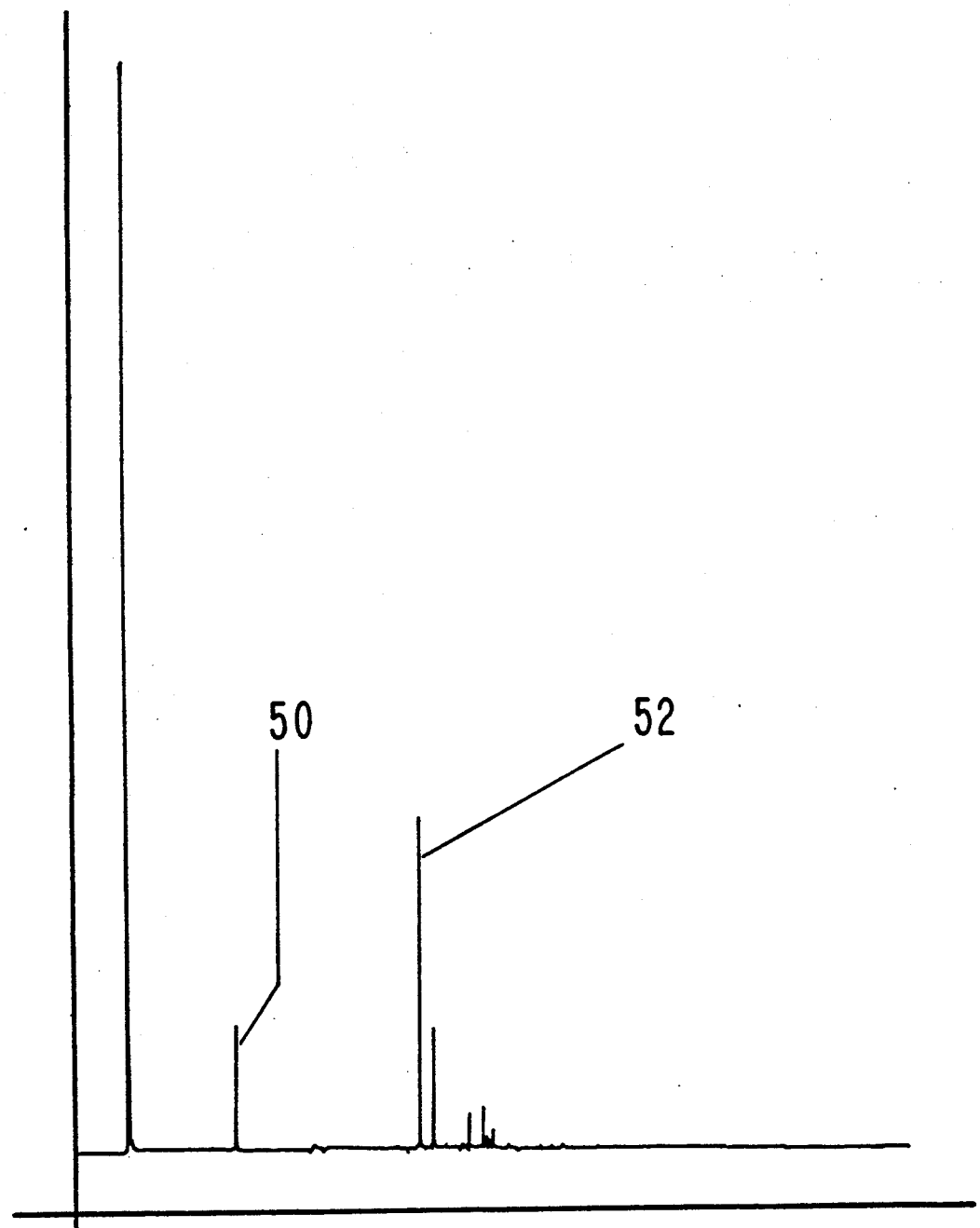

FIG. 5 is the GLC profile for the reaction product of Example II containing the compound having the structure:

(Conditions: 30 meters×0.32mm fused silica capillary SPB-1 column programmed from 120°–220° C. at 8° C. per minute).

The peak indicated by reference numeral 50 is the peak for the compound having the structure:

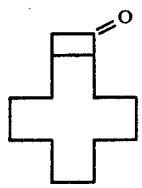

The peak indicated by reference numeral 52 is the peak for the compound having the structure:

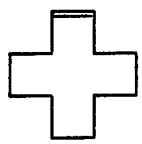

FIG. 6 is the infra-red spectrum for the compound having the structure:

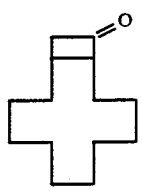

prepared according to Example II.

FIG. 7 is the NMR spectrum for the compound having the structure:

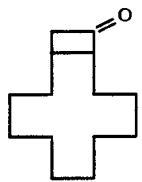

prepared according to Example II.

THE INVENTION

It has now been determined that the compound having the structure:

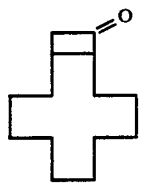

(also known as the bicyclo[10.2.0]tetradecan-13-one of our invention) is capable of imparting musky and earthy aromas with minty green and camphoraceous topnotes to perfume compositions, colognes and perfumed articles including but not limited to solid or liquid anionic, cationic, nonionic or zwitterionic detergents, fabric softener compositions, fabric softener articles, hair preparations, cosmetic powders and perfume polymers. Our invention also contemplates an intermediate used in synthesizing the compound having the structure:

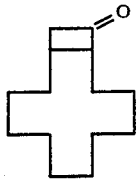

which intermediate has the structure:

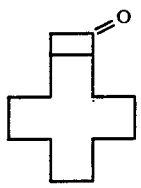

The bicyclo[10.2.0]tetradecan-13-one of our invention having the structure:

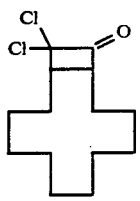

is prepared according to a two step reaction; the first is a reaction of cyclododecene having the structure:

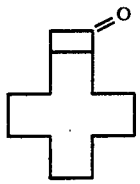

with alpha, alpha, alpha-trichloroacetylchloride according to the reaction:

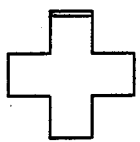

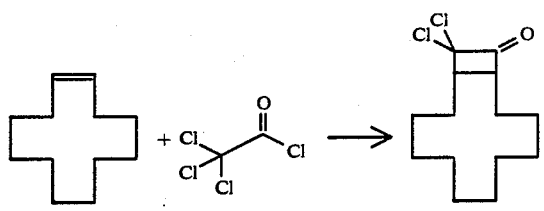

The resulting product having the structure:

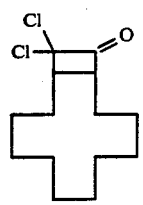

is then reacted with zinc and ammonium chloride according to the reaction:

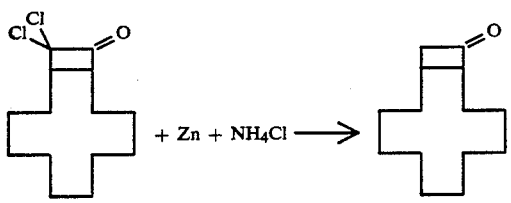

The resulting product the bicyclo[10.2.0]tetradecan-13-one of our invention has a musky and earthy aroma with minty, green and camphoraceous topnotes.

Accordingly our invention encompasses the genus of compounds defined according to the structure:

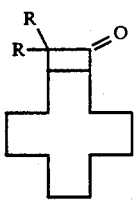

wherein R represents hydrogen or chloro.

In carrying out the reaction:

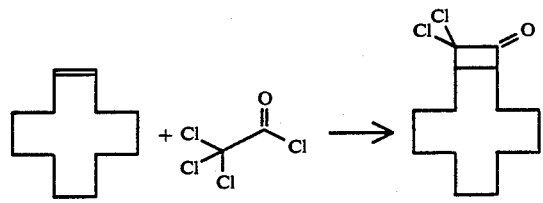

this reaction takes place using an activated zinc catalyst (e.g., zinc and copper).

Actually, the complete reaction sequence for producing the dichloro derivative is as follows:

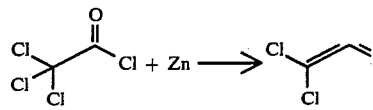

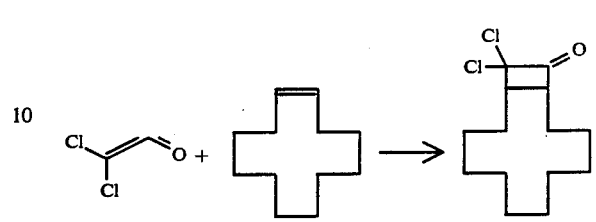

The reaction takes place in the presence of a solvent such as the dimethyl ether of ethylene glycol admixed with diethyl ether. The reaction temperature is at reflux conditions, e.g. from about 40° C. up to about 45° C. and the reaction takes place over a period of between about 5 and about 20 hours. At the end of the reaction, the resulting product having the structure:

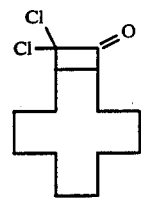

is concentrated for use in the next reaction.

With respect to the reaction to wit:

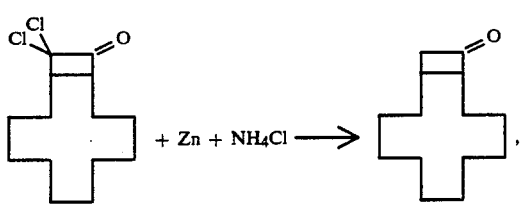

this reaction takes place at a temperature in the range of from about 55° C. up to about 75° C. at reflux conditions. The reaction is carried out in the presence of an inert solvent under anhydrous conditions; and a suitable solvent is anhydrous methyl alcohol.

At the end of the reaction, the reaction product is washed and distilled using a fractional distillation column (boiling point: 138° C. at 3 mm Hg; or 305° C. at one atmosphere pressure).

The bicyclo[10.2.0 tetradecan-13-one of our invention can be used to contribute musky and earthy aromas with minty, green and camphoraceous topnotes to perfume compositions, colognes and perfumed articles. As olfactory agents the bicyclo[10.2.0]tetradecan-13-one of our invention can be formulated into or used as a component of a "perfume composition".

The term "perfume composition" is used herein to mean a mixture of organic compounds including, for example, alcohols, aldehydes, ketones (other than the ketone of our invention), nitriles, esters and frequently hydrocarbons which are admixed so that the combined odors of the individual components produce a pleasant and desired fragrance. Such perfume conditions usually contain: (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of bicyclo[10.2.0]tetradecan-13-one of our invention which will be effective in perfume compositions depends on many factors, including the other ingredients, their amounts and the effects which are desired. It has been found that perfume compositions containing as little as 0.05% and as much as 5% of the bicyclo[10.2.0]tetradecan-13-one of our invention can be used to impart, augment or enhance musky and earthy aromas with minty, green and camphoraceous topnotes to soaps, cosmetics, solid or liquid anionic, cationic, nonionic or zwitterionic detergents and other products, including perfumed polymers. The amount employed can range up to 50% of the fragrance and can be as low as 1% of the original fragrance and will depend on considerations of cost, nature of the end product, the effect desired in the finished product and the particular fragrance sought.

The bicyclo[10.2.0]tetradecan-13-one of our invention can be used alone or in a perfume composition as an olfactory component in detergents, soaps, space odorants and deodorants, perfumes, colognes, toilet waters, bath salts, hair preparations such as lacquers, brilliantines, pomades, and shampos, cosmetic preparations such as creams, deodorants, hand lotions and sun screens, powders such as talcs, dusting powders, face powder, and the like. When used as an olfactory component of a perfumed article, as little as 0.05% of the bicyclo[10.2.0]tetradecan-13-one of our invention will suffice to impart musky and earthy aromas with minty, green and camphoraceous topnotes. Generally no more than 5.0% is required.

In addition, the perfumes composition can contain a vehicle or carrier for the bicyclo[10.2.0]tetradecan-13-one of our invention. The vehicle can be a liquid such as an alcohol such as ethanol, a glycol such as propylene glycol, or the like. The carrier can be an absorbent solid such as a gum (e.g. guar gum or xanthan gum) or a microporous polymer or components for encapsulating the composition such as by means of coacervation.

The following Examples I and II are given to illustrate techniques for producing the bicyclo[10.2.0]tetradecan-13-one of our invention. Examples following Example II, that is, Examples III and onward are given to illustrate embodiments of our invention concerning the use of the bicyclo[10.2.0]tetradecan-13-one for its organoleptic properties. It will be understood that these examples are illustrative and that the invention is not to be considered restricted except as indicated in the appended claims.

EXAMPLE i

Process For Preparing
14,14-Dichlorobicyclo[10.2.0]Tetradecan-13-one

Reaction

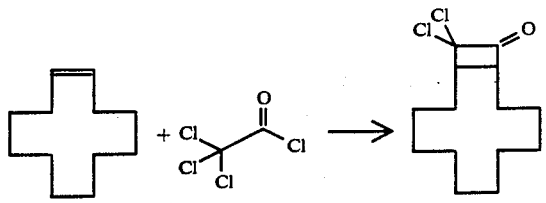

Into a 300 ml reaction flask equipped with stirrer, thermometer, reflux condenser, heating mantle, addition funnel and drying tube equipped with dry nitrogen inlet is placed 100 ml anhydrous diethyl ether and 75 ml of the dimethyl ether of ethylene glycol. While maintaining the reaction mass temperature at 19° C., with stirring, 5 grams of activated zinc (a zinc copper mixture) is added to the reaction mass.

While maintaining the reaction mass at 19° C., 8.3 grams (0.05 moles) of cyclododecene is added to the reaction mass.

While maintaining the reaction temperature at 20°-24° C. over a period of one hour, 12.7 grams (7.8 ml) (0.07 moles) of alpha, alpha, alpha-trichloroacetylchloride is added dropwise to the reaction mass with stirring.

The reaction mass is then heated to reflux and refluxed at a temperature of 42° C. for a period of 35 hours.

At the end of the 35 hour reflux period, the reaction mass is filtered and concentrated and then washed with 7% sodium bicarbonate followed by water. The reaction mass is then dried.

Figure 1:
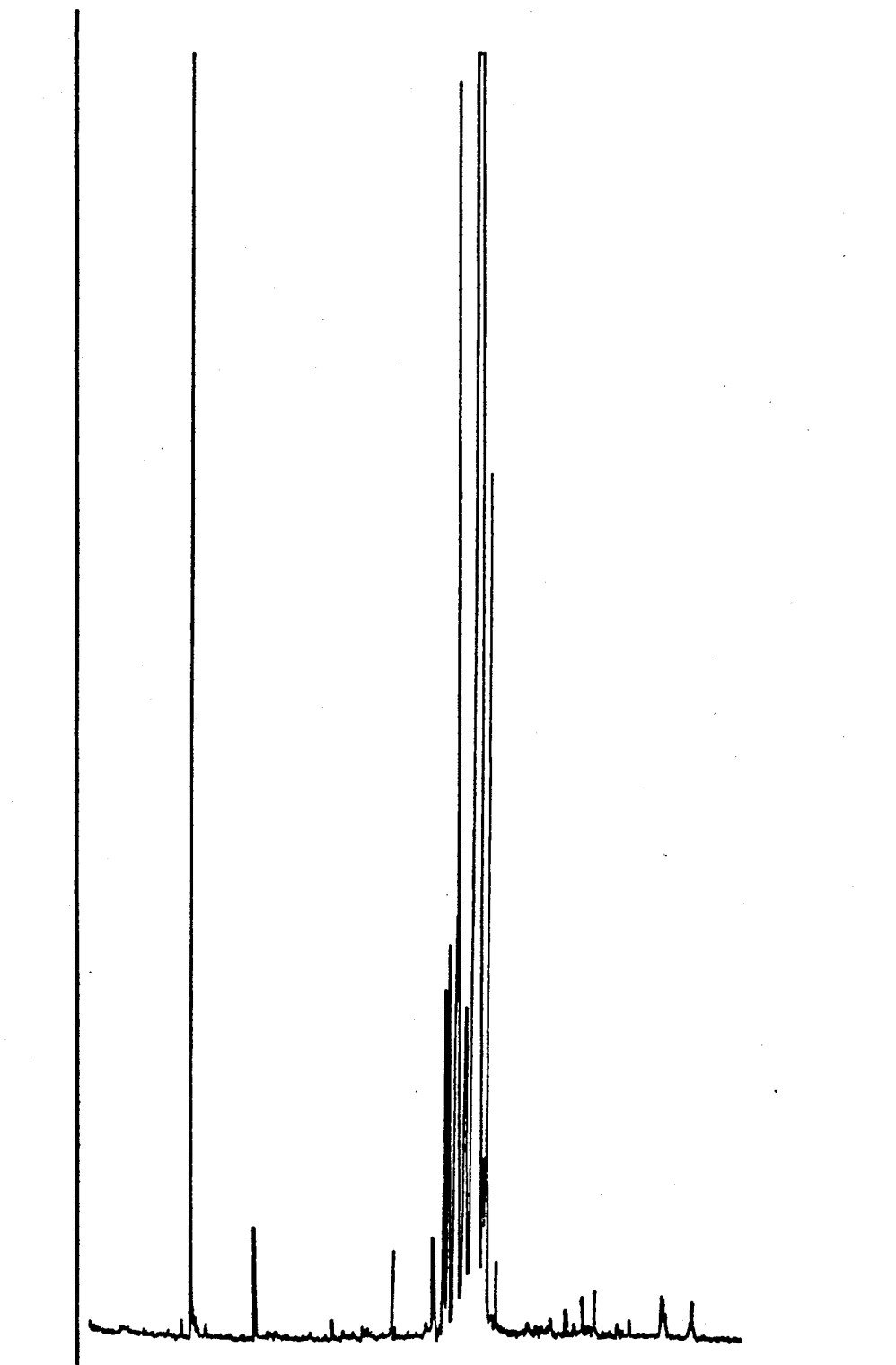
FIG. 1 is the GLC profile for the reaction product of Example I containing the compound having the structure.

FIG. 1 is the GLC profile of the reaction product containing the compound having the structure:

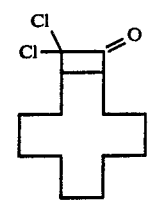

FIG. 2 is the GC having mass spectrum of the compound having the structure:

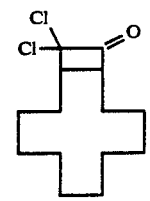

FIG. 3 is the infra-red spectrum of the compound having the structure:

FIG. 4 is the NMR spectrum of the compound having the structure:

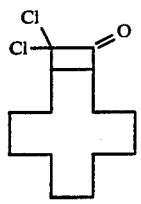

The compound having the structure:

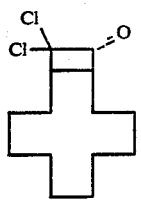

is then utilized in Example II.

EXAMPLE II

Preparation of Bicyclo[10.2.0] Tetradecan-13-One

Reaction

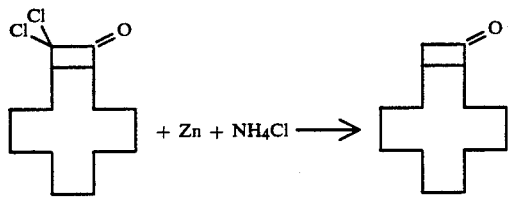

Into a 250 ml, 4 neck flask equipped with mechanical stirrer, "Y" tube with reflux condenser, pot thermometer and nitrogen inlet is placed 12.9 grams of the compound having the structure:

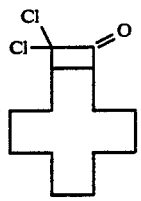

prepared according to Example I. 100 Ml anhydrous methyl alcohol is added to the reaction mass causing it to dissolve.

The resulting solution while being maintained at 25°–29° C. is admixed with 5 grams (0.07645 moles) of zinc dust.

The reaction mass is then cooled using a cooling bath to 27° C. One gram of ammonium, chloride is added to the reaction mass with stirring. The reaction mass exotherms to 37°–39° C. The reaction mass is then heated to 64° C. (reflux) and is refluxed at 64° C. for a period of 2 hours.

The reaction mass is then cooled and filtered.

The filtrate is admixed with 500 ml water and then acidified with 3 m of 6 molar hydrochloric acid to a pH of 1.5. The organic material is extracted with 60 ml methylene dichloride resulting in two phases; an organic phase and an aqueous phase. The organic phase is then separated and washed with one 150 ml portion of water followed by one 50 ml portion of saturated sodium chloride. The resulting product is filtered through anhydrous sodium sulfate and distilled. The product having the structure:

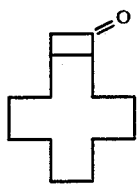

is distilled on a fractionation column at 138° C. at a vacuum of 3mm Hg.

The product having the structure:

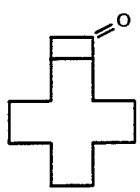

(bulked fractions 5–7) has a musky and earthy aroma profile with minty, green and camphoraceous topnotes.

FIG. 5 is the GLC profile of the reaction product prior to distillation. The peak indicated by reference numeral 50 is the peak for cyclododecene. The peak indicated by reference numeral 52 is the peak for the compound having the structure:

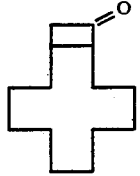

FIG. 6 is the infra-red spectrum for the compound having the structure:

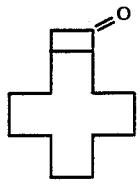

FIG. 7 is the NMR spectrum for the compound having the structure:

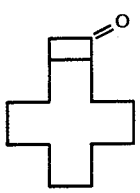

EXAMPLE III

Perfume Formulation

The following vetiver perfume formulation is prepared:

| Ingredients | Parts by Weight |
| --- | --- |
| Vetivone | 25.0 |
| Vetiverol | 5.0 |
| Musk Ketone | 8.0 |
| Styrax essence | 12.5 |
| Compound having the structure: <br /> 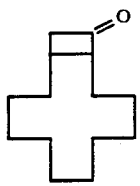 <br /> prepared according to Example II, bulked distillation fractions 5-7 | 25.0 |

The addition of the compound having the structure:

prepared according to Example II imparts to this vertiver formulation musky and earthy undertones and minty green and camphoraceous topnotes. Accordingly, the aroma of the formulation may be described as: "vertiver with musky and earthy undertones and minty, green and camphoraceous topnotes."

EXAMPLE IV

Perfumed Liquid Detergent

Concentrated liquid detergents with aromas as described in Table I below (which detergents are produced from the lysine salt of n-dodecyl benzene sulfonic acid as more specifically described in U.S. Letters Patent 3,948,818 issued on Apr. 6, 1976) the specification for which is incorporated by reference herein are prepared containing one of the substances set forth in Table 1 below. They are prepared by adding and homogeneously mixing the appropriate quantity of substance as indicated in Table I below. The detergents all possess aroma profiles as set forth in Table I below, the intensity increasing with greater concentrations of the composition of matter as set forth in Table I below:

TABLE I

| Aroma Ingredient | Aroma Profile |
| --- | --- |
| The compound having the structure: (structure) prepared according to Example II, bulked distillation fractions 5-7 | A musky and earthy aroma with minty, green and camphoraceous topnotes. |
| Perfume composition of Example III | Vetiver with musky and earthy undertones and minty, green and camphoraceous topnotes. |

EXAMPLE V

Preparation of a Cologne and Handkerchief Perfume

Aroma imparting and augmenting ingredients as defined according to Table I in Example IV are incorporated into cologne at concentrations of 1.5%, 2.0%, 2.5%, 3.0%, 4.0% and 5.0%, in 75%, 80%, 85%, 90% and 95% solutions of aqueous ethanol; and into handkerchief perfumes at concentrations of 15%, 20%, 25% and 30% (in 80%, 85% and 95% aqueous ethanol solutions). The use of the compositions of matter as set forth in Table I of Example IV affords distinct and definitive aroma profiles as set forth in Table I of Example IV to the handkerchief perfumes and to the colognes.

EXAMPLE VI

Preparation of a Soap Composition

One hundred grams of soap chips (IVORY ® manufactured by the Procter & Gamble Company of Cincinnati, Ohio) are melted and intimately admixed with one of the aroma materials as set forth in Table I of Example IV, supra, the amount of composition of matter of Table I of Example IV being one gram of each composition of matter. The conditions of mixing are 180° C., 3 hours, 12 atmospheres pressure. At the end of the mixing cycle, while the soap is still under 12 atmospheres pressure, the mixture of soap and perfume ingredient is cooled to room temperature. At this temperature, the resulting mixture is in a solid state. The resulting soap block is then cut up into soap cakes. Each of the soap cakes manifests an excellent aroma as set forth in Table I of Example IV. None of the soap samples shown any discoloration even after two weeks in the oven at 90° F.

EXAMPLE VII

Preparation of a Detergent Composition

A total of 100 grams of a detergent powder (nonionic detergent powder containing a proteolytic enzyme prepared according to Example I of Canadian Patent 985,190 issued on Mar. 9, 1976) is mixed with 0.15 grams of one of the compositions of matter as set forth in Table I of Example IV until a substantially homogeneous composition is obtained. Each of the compositions has excellent aroma profiles as set forth in Table I of Example IV.

EXAMPLE VIII

Perfumed Liquid Detergents

Concentrated liquid detergents with rich, pleasant aromas as set forth in Table I of Example IV are prepared containing 0.10%, 0.15% and 0.20% of each of the compositions of matter set forth in Table I of Example IV. They are prepared by adding and homogeneously admixing the appropriate quantity of composition of matter of Table I of Example IV in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table I of Example IV, the intensity increasing with greater concentrations of composition of matter of Table I of Example IV.

What is claimed is:

1. The compound defined according to the structure:

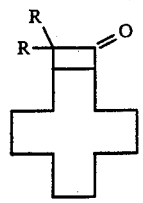

wherein R is hydrogen or chloro.

2. The product of claim 1 wherein R is chloro.
3. The product of claim 1 wherein R is hydrogen.
4. The process for augmenting or enhancing the aroma of a perfume composition, cologne or perfumed article comprising the step of adding to said perfume composition cologne or perfumed article an aroma augmenting or enhancing quantity of the compound defined according to claim 3.

* * * * *